United States Patent [19]

Baker et al.

[11] 4,335,131

[45] Jun. 15, 1982

[54] AMRINONE-N-GLUCURONIDE, SALTS AND CARDIOTONIC USE THEREOF

[75] Inventors: James F. Baker, East Greenbush; Bernard W. Chalecki, Jr., Sand Lake, both of N.Y.

[73] Assignee: Sterling Drug Inc., New York, N.Y.

[21] Appl. No.: 209,393

[22] Filed: Nov. 24, 1980

[51] Int. Cl.$^3$ .................... A61K 31/44; C07D 405/14
[52] U.S. Cl. .................... 424/263; 546/256; 424/180; 536/23
[58] Field of Search .................... 536/23, 24, 22, 18; 424/180, 263; 546/256

[56] References Cited

U.S. PATENT DOCUMENTS 2,384,102  9/1945  Lee et al. .................... 536/22
4,004,012  1/1977  Lesher .................... 424/263
4,072,746  2/1978  Opalka, Jr. .................... 424/263

OTHER PUBLICATIONS

The Carbohydrates, Edited by Ward Pigman, pp. 406–419, Academic Press Inc., New York, 1957.

*Primary Examiner*—Blondel Hazel
*Attorney, Agent, or Firm*—Robert K. Bair; B. Woodrow Wyatt

[57] ABSTRACT

Amrinone-N-glucuronide or pharmaceutically-acceptable acid-addition or cationic salt thereof useful as cardiotonic agent is prepared by reacting amrinone with glucuronic acid or cationic salt thereof. Cardiotonic composition and method for increasing cardiac contractility using said amrinone-N-glucuronide or salt as active component are disclosed.

5 Claims, No Drawings

AMRINONE-N-GLUCURONIDE, SALTS AND CARDIOTONIC USE THEREOF

BACKGROUND OF THE INVENTION (a) Field of the Invention

This invention relates to amrinone-N-glucuronide, useful as a cardiotonic agent, and to its preparation.

(b) Description of the Prior Art

Lesher and Opalka U.S. Pat. Nos. 4,004,012, issued Jan. 18, 1977, and 4,072,746, issued Feb. 7, 1978] show inter alia, as a cardiotonic agent 3-amino-5-(4-pyridinyl)-2(1H)-pyridinone now generically known as amrinone and its corresponding 3-(lower-alkanoylamino)-5-(4-pyridinyl)-2(1H)-pyridinone derivatives, which are prepared by reacting said 3-amino compound with a lower-alkanoylating agent.

SUMMARY OF THE INVENTION

In a composition of matter aspect, the invention resides in amrinone-N-glucuronide, that is, 3-glucuronoylamino-5-(4-pyridinyl)-2(1H)-pyridinone or pharmaceutically acceptable acid-addition or cationic salt thereof, which is useful as a cardiotonic agent.

Another composition of matter aspect of the invention relates to amrinone-N-glucuronide in solid form or pharmaceutically-acceptable acid-addition or cationic salt thereof, useful as a cardiotonic agent.

The invention is a process aspect resides in process of producing amrinone-N-glucuronide which comprises reacting 3-amino-5-(4-pyridinyl)-2(1H)-pyridinone with glucuronic acid or cationic salt thereof.

A composition aspect of the invention resides in a cardiotonic composition for increasing cardiac contractility in a patient, said composition comprising a pharmaceutically-acceptable carrier and, as the active component thereof, a cardiotonically-effective amount of amrinone-N-glucuronide or pharmaceutically-acceptable acid-addition or cationic salt thereof.

In a method aspect, the invention resides in a method for increasing cardiac contractility in a patient requiring such treatment which comprises administering to such patient a medicament comprising a pharmaceutically-acceptable carrier and, as the active component thereof, a cardiotonically-effective amount of amrinone-N-glucuronide or pharmaceutically-acceptable acid-addition or cationic salt thereof.

DETAILED DESCRIPTION INCLUSIVE OF PREFERRED EMBODIMENTS

In a composition of matter aspect the invention resides in amrinone-N-glucuronide, alternatively named 3-glucuronyl-5-(4-pyridinyl)-2(1H)-pyridinone or 1-deoxy-1-[(1,6-dihydro-6-oxo-[3,4'-bipyridin]-5-yl)amino]-β-D-glucopyranuronic acid having the formula I

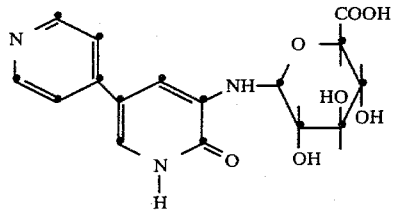

or pharmaceutically-acceptable acid-addition or cationic salt thereof. This compound is useful as a cardiotonic agent, as determined by standard pharmacological evaluation procedures. We originally isolated this compound as one of a number of metabolites of amrinone in dogs and monkeys. Since glucuronide derivatives or pharmaceuticals normally do not possess the pharmaceutical activity of their parent drug, the cardiotonic utility of the instant amrinone-N-glucuronide was unexpected.

Another composition of matter aspect of the invention resides in amrinone-N-glucuronide in solid form or pharmaceutically-acceptable acid-addition or cationic salt thereof, useful as a cardiotonic agent.

In a process aspect the invention resides in the process of reacting amrinone with glucuronic acid or cationic salt thereof to produce amrinone-N-glucuronide and isolating amrinone-N-glucuronide in solid form.

A composition aspect of the invention resides in a cardiotonic composition for increasing cardiac contractility, said composition comprising a pharmaceutically-acceptable carrier and, as the active component thereof, a cardiotonically-effective amount of amrinone-N-glucuronide or pharmaceutically-acceptable acid-addition or cationic salt thereof. A preferred embodiment of said composition has amrinone-N-glucuronide as the active component.

A method aspect of the invention resides in the method for increasing cardiac contractility in a patient requiring such treatment which comprises administering orally or parenterally in a solid or liquid dosage form to such patient a cardiotonically-effective amount of amrinone-N-glucuronide or pharmaceutically-acceptable acid-addition or cationic salt thereof. In a preferred embodiment of said method amrinone-N-glucuronide is administered.

Amrinone-N-glucuronide of the invention is useful both in the free base form and in the form of its acid-addition salt, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salt, that is, salts whose anions are relatively innocuous to the animal organism in pharmaceutical doses of the salts, so that the beneficial cardiotonic properties inherent in the free base are not vitiated by side effects ascribable to the anions. In practicing the invention, it was convenient to use amrinone-N-glucuronide in free base form. However, appropriate pharmaceutically-acceptable salts within the scope of the invention are those derived from mineral acids such as hydrochloric acid, sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate respectively.

The acid-addition salts of said compound of the invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said compounds are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

Other pharmaceutically-acceptable salts of said compound of formula I are those cationic salts derived from strong inorganic or organic bases, e.g., sodium hydroxide, potassium hydroxide, trimethylammonium hydroxide, to produce the O-cationic salt of the carboxylic acid group of the glucopyranuronic acid moiety. Also, the compound of formula I can react with a second mole of said strong base to form the corresponding 1- or N-cationic salt, e.g., sodium, potassium, trimethylammonium salt, respectively, that is, the cationic ion being attached to the 1- or N-position of the 2(1H)-pyridinone ring.

The molecular structures of the compounds of the invention were assigned on the basis of evidence provided by infrared, nuclear magnetic resonance and mass spectra, and by the correspondence of calculated and found values for elemental analyses.

The manner of making and using the instant invention will now be generally described so as to enable a person skilled in the art of pharmaceutical chemistry to make and use the same, as follows.

The reaction of amrinone with glucuronic acid or cationic salt thereof was carried out by mixing the reactants in aqueous medium, preferably at a slightly acidic pH of about 5.5 to 6.5, either at room temperature or by heating the reaction mixture at about 50° to 100° C., preferably about 70° to 80° C. The reaction was conveniently carried out by mixing a weakly acidic aqueous solution of amrinone containing enough acetic acid to dissolve the amrinone with an aqueous solution containing molar equivalent quantities of glucuronolactone and sodium hydroxide, and then allowing the slightly acidic reaction mixture, adding acetic acid if necessary, to stand at room temperature until the reaction is complete or, alternatively, heating the reaction mixture to facilitate the reaction. Alternatively, there can be used in place of sodium hydroxide other bases, e.g., potassium hydroxide, ammonium hydroxide, trimethylammonium hydroxide, and the like, provided the resulting cationic salt of glucuronic acid is soluble in the slightly acidic aqueous reaction mixture.

The following examples will further illustrate the invention without, however, limiting it thereto.

EXAMPLE 1

Amrinone-N-glucuronide, alternatively named 3-glucuronyl-5-(4-pyridinyl)-2(1H)-pyridinone or 1-deoxy-1-[(1,6-dihydro-6-oxo-[3,4'-bipyridin]-5-yl]amino]-β-D-gluccopyranuronic acid-A 2.0 g. portion of amrinone (10.7 m. mole) i.e., 3-amino-5-(4-pyridinyl)-2(1H)-pyridinone or 5-amino-[3,4'-bipyridin]-6(1H)-one, was suspended in 100 ml. of distilled water and to the suspension was added dropwise with stirring glacial acetic acid until complete solution was achieved. A 2.0 g. portion of glucuronolactone (11.4 m. mole) and 0.45 g. of sodium hydroxide (11.4 m. mole) were dissolved in 20 ml. of water and the resulting solution was stirred for one hour at room temperature. The two solutions were then mixed, one ml. of acetic acid was added and the resulting solution (pH of about 6) was heated with stirring at 70°-80° C. for one hour and then stirred at room temperature overnight. The separated precipitate was collected and dried in a vacuum desiccator over anhydrous calcium sulfate to yield 2.2 g. of amrinone-N-glucuronide. TLC examination [solvent: acetonitrile (80)/water(20)] of the product dissolved in water with a few drops of isopropyl amine indicated that the product was about 95% pure N-glucuronide of amrinone. NMR and mass spectral analyses of the product showed spectra consistent with that of the assigned structure.

EXAMPLE 2

Amrinone-N-glucuronide—To a solution containing 34.8 g. of sodium hydroxide (0.852 mole) dissolved in 1500 ml. of water was added 150 g. of glucuronolactone (0.852 mole) and the resulting solution was stirred at room temperature for three hours. This solution was then poured with stirring into a solution containing 150 g. of amrinone 0.806 mole, 7.5 liters of water and about 200 ml. of acetic acid. The resulting reaction mixture was stirred at room temperature over the weekend (three days). The heavy yellow precipitate was collected, washed successively with water, isopropyl alcohol and ether, and dried in vacuo at 40° C. to produce 233 g. of amrinone-N-glucuronide which was found to contain 2.8% water. The product was first dried at 50° C. over the weekend (still had 2.1% water) and was then dried at 100° C. in high vacuum (about 1 mm) to produce 220 g. of amrinone-N-glucuronide, m.p. 225°-240° C. The NMR and mass spectra of this product were consistent with the assigned structure and with corresponding spectra found for amrinone-N-glucuronide isolated from dog urine as a metabolic product of amrinone administered orally.

Acid-addition salts of amrinone-N-glucuronide are conveniently prepared by adding to a mixture of 0.5 g. of amrinone-N-glucuronide in about 10 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., methanesulfonate, sulphate, phosphate, respectively. Also, the acid-addition salt is conveniently prepared in aqueous solution by adding to water with stirring molar equivalent quantities of amrinone-n-glucuronide and the appropriate acid, e.g., lactic acid or hydrochloric acid, to prepare respectively the lactate or hydrochloride salt of amrinone-N-glucuronide in aqueous solution.

The usefulness of amrinone-N-glucuronide or salt as a cardiotonic agent is demonstrated by its effectiveness in standard pharmacological test procedures, for example, in causing a significant increase in the contractile force of the isolated cat or guinea pig atria and papillary muscle or in causing a significant increase in the cardiac contractile force in the anesthetized dog with low or minimal changes in heart rate and blood pressure. The isolated cat atria and papillary muscle procedure and the anesthetized dog procedure have been described, e.g., in U.S. Pat. No. 4,072,746, issued February 7, 1978. The isolated guinea pig atria and papillary muscle procedure and its comparison with said cat atria and papillary muscle procedure are presented as follows.

Cat or guinea pig atria papillary muscle test—Cats of either sex weighing 0.6 to 2.7 kg. were anesthetized with sodium pentobarbital, 30 mg./mg. i.v. and exsanguinated. Hartley guinea pigs of either sex weighing 650 to 800 g. were stunned with a sharp blow to the head and exsanguinated. Both cats and guinea pigs and their tissues were handled by the following procedures. The chest was opened rapidly, the heart excised, rinsed in Tyrode's solution, and the right atrium and one or more small thin right ventricular papillary muscles were excised. The tissues were transferred to a large Petri dish filled with modified Tyrode's solution oxygenated with 95% $O_2$, 5% $CO_2$. A silver wire was attached to each of two opposite ends of the papillary muscle or the atrial preparation. The wire from the nontendonous end of the papillary muscle was attached to a glass covered platinum electrode which was connected to the cathode of a Grass Model $SD_5$ stimulator. The pouch end of the atrium was attached to the curved end of a glass rod. The preparations were mounted in organ baths (40 ml. for papillary muscles and 50 ml. for atrial) filled with modified Tyrode's solution maintained at 37° C. and oxygenated with 95% $O_2$, 5% $CO_2$. The wire on the tendonous end of the papillary muscle was looped and tied to a force-displacement transducer (Grass, FTO3C) and then connected to the anodal terminal of the stimulator. The second wire on the right atrium was tied to a force-displacement transducer and the atrium allowed to beat spontaneously. The transducer is connected to a Grass model 7 polygraph. The resting tension on each muscle was adjusted to produce a maximum contractile force (Starlings Law) and the muscle stimulated electrically at a rate of 120 beats/min. by a suprathreshold (1.5×threshold) rectangular pulse, 0.5 msec in duration.

After Starlings and voltage adjustment, the preparations were washed and allowed to equilibrate for 15 minutes before a test dose of dopamine (1.0 µg./ml.) or isoproterenol (0.0003 µg./ml.) was added and the response monitored. Next, the test drug dissolved in vehicle or the vehicle alone was added to the tissue baths and the responses recorded. The tissues were washed at least two times after each dose or until the pre-drug control level in developed tension and rate was obtained. Five or six doses of drug were given to the preparations over a period of 4–5 hours.

The modified Tyrode's solution bathing the preparation had the following composition (in mM): NaCl, 136.9; KCl, 5.4; $NaH_2PO_4$, 0.4; $CaCl_2$, 1.8; $MgCl_2.6H_2O$, 1.0; $NaHCO_3$, 11.9 glucose, 5.5; EDTA, 0.04. The solution was equilibrated with a gas mixture consisting of 95% $O_2$ and 5% $CO_2$, and the pH was 7.3–7.4 at 37° C.

Tissue Differences—A comparison of cat and guinea pig tissue characteristics is presented as follows: The cat papillary muscles used averaged 5.12±0.20 mm in length and weighed 7.01±0.64 mg. with a mean cross sectional area of 1.31 $mm^2$ (N=26, N being the number of preparations). Guinea pig papillary muscles averaged 6.60±0.18 mm in length and weighed 9.09±0.47 mg. Their mean cross sectional area was 1.31 $mm^2$ (N=60). The resting tension (tension applied to the muscle to obtain maximum contractile force, Starling's Law) applied to cat papillary muscles averaged 1.5±0.09 g. (N=34) while the resting tension applied to guinea pig papillary muscles was 1.01±0.042 g. (N=56). Cat papillary muscle control active tension at the start of the day averaged 0.62±0.05 g. (N=34); the guinea pig papillary muscles averaged 0.213±0.011 g. (N=62). A comparison of cat and guinea pig papillary muscle active tension per mg. of tissue $$\left(\frac{\text{control active tension in mg}}{\text{wet weight of tissue in mg}}\right)$$

indicated that for their weight cat papillary muscles are almost 4 times stronger than guinea pig papillary muscles. The cat right atria weighed more than guinea pig right atria; 306±15 mg. (N=24) and 76.5±mg. (N=41) respectively. The average right atrial rate for cat atria was 133±3 beats/min. (n=34) while the rate for guinea pig atria was 167±3 beats/min. (n=57). The applied resting tension on guinea pig atria averaged 1.95±0.06 g. (N=117); on cat right atria the resting tension averaged 2.21±0.10 g. (N=34). A comparison of guinea pig and cat right atrial control active tension indicates that, similar to the papillary muscles form the two species, the cat muscle was stronger; 1.93±0.10 g. (N=34) active tension for cat atria and 0.742±0.04 g. (N=34) active tension for guinea pig atria. Because of the lower control active tensions of guinea pig tissues the percent change from control values for both rate and force responses is elevated. Thus, whereas cardiotonic activity is ascertained with a papillary muscle force or right atrial force increase of 26% and greater in the cat test, corresponding activity in the guinea pig test is designated with a papillary muscle force or right atrial force increase of 31% and greater.

When tested by said isolated guinea pig atria and papillary muscle procedure, amrinone-N-glucuronide or salt when tested at doses of 10, 30 and 100 µg./ml., was found to cause significant increase, that is, greater than 30%, in papillary muscle force and a significant increase, that is, greater than 30%, in right atrial force, while causing a lower percentage increase per dose in right atrial rate than the percentage increase in right atrial or papillary muscle force. For example, amrinone-N-glucuronide when tested by said procedure at 10, 30 and 100 µg./ml. was found to cause a papillary muscle increase of 39%, 52% and 63%, respectively, and corresponding right atrial force increases of 24%, 41% and 73%, respectively.

The present invention includes within its scope a cardiotonic composition for increasing cardiac contractility, said composition comprising a pharmaceutically-acceptable carrier and, as the active component thereof, a cardiotonically-effective amount of amrinone-N-glucuronide or pharmaceutically-acceptable acid-addition or cationic salt thereof. The invention also includes within its scope the method for increasing cardiac contractility in a patient requiring such treatment which comprises administering to such patient a cardiotonically-effective amount of amrinone-N-glucuronide or pharmaceutically-acceptable acid-addition or cationic salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueousorganic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, perserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. Amrinone-N-glucuronide or pharmaceutically-acceptable acid-addition or cationic salt thereof.

2. A cardiotonic composition for increasing cardiac contractility, said composition comprising a pharmaceutically-acceptable inert carrier and, as the active component thereof, a cardiotonically-effective amount of amrinone-N-glucuronide or pharmaceutically-acceptable acid-addition or cationic salt thereof.

3. A composition according to claim 2 where the active component is amrinone-N-glucuronide.

4. The method for increasing cardiac contractility in a patient requiring such treatment which comprises administering orally or parenterally in a solid or liquid dosage form to such patient a cardiotonically-effective amount of amrinone-N-glucuronide or pharmaceutically-acceptable acid-addition or cationic salt thereof.

5. The method according to claim 4 where amrinone-N-glucuronide is administered.

* * * * *

UNITED STATES PATENT AND TRADEMARK OFFICE
CERTIFICATE OF CORRECTION

PATENT NO. : 4,335,131
DATED : June 15, 1982
INVENTOR(S) : J.F. Baker et al.

It is certified that error appears in the above–identified patent and that said Letters Patent are hereby corrected as shown below:

Column 2, line 4, "or" should read -- of --.

Column 4, line 50, "amrinone-n-" should read -- amrinone-N- --.

Signed and Sealed this

First Day of February 1983

[SEAL]

Attest:

GERALD J. MOSSINGHOFF

Attesting Officer     Commissioner of Patents and Trademarks